United States Patent [19]

Ichinohe et al.

[11] Patent Number: 5,310,842

[45] Date of Patent: * May 10, 1994

[54] HIGHER ALKOXY-SUBSTITUTED ORGANOPOLYSILOXANE

[75] Inventors: Shoji Ichinohe; Syuichi Arai, both of Gunma, Japan

[73] Assignee: Shin-Etsu Chemical Co., Ltd., Tokyo, Japan

[*] Notice: The portion of the term of this patent subsequent to Sep. 15, 2009 has been disclaimed.

[21] Appl. No.: 46,287

[22] Filed: Apr. 14, 1993

Related U.S. Application Data

[63] Continuation-in-part of Ser. No. 973,530, Nov. 9, 1992, abandoned, which is a continuation of Ser. No. 759,340, Sep. 13, 1991, abandoned.

[30] Foreign Application Priority Data

Sep. 14, 1990 [JP] Japan .................................. 2-245944

[51] Int. Cl.$^5$ ............................................. C08G 77/08
[52] U.S. Cl. .................................... 528/12; 528/15; 528/29; 528/31; 556/457
[58] Field of Search .................. 528/15, 12, 29, 31; 556/457

[56] References Cited

U.S. PATENT DOCUMENTS

| | | | |
|---|---|---|---|
| 2,967,171 | 1/1961 | Baines et al. | 528/29 |
| 3,354,101 | 11/1967 | Williams et al. | 528/29 |
| 3,541,127 | 11/1970 | Beattie et al. | 528/29 |
| 3,958,073 | 5/1976 | Trevisan et al. | 528/25 |
| 4,049,873 | 9/1977 | Creasey et al. | 428/447 |
| 4,102,860 | 7/1978 | Wohlfarth et al. | 528/18 |
| 4,454,262 | 6/1984 | Fukayama et al. | 525/477 |
| 4,501,872 | 2/1985 | Chang et al. | 528/34 |
| 4,731,411 | 3/1988 | Lucas | 524/860 |
| 4,797,445 | 1/1989 | Piskoti | 528/34 |
| 5,147,965 | 9/1992 | Ichinohe et al. | 528/12 |

FOREIGN PATENT DOCUMENTS 0019837 12/1980 European Pat. Off. .
0090382 10/1983 European Pat. Off. .
2299379 8/1976 France .

OTHER PUBLICATIONS

World Patents Index, Section Ch. Week 12, Derwent Publications, Ltd., London, GB, No. 72-19816T.
CA 80:63762x (Mar. 25, 1974).
Kohama et al., "Alcoholysis of Poly(methylhydrogensiloxane)," Journal of Applied Polymer Science, vol. 21, No. 3, pp. 863-867 (Mar. 1977).

*Primary Examiner*—John C. Bleutge
*Assistant Examiner*—Margaret W. Glass
*Attorney, Agent, or Firm*—Millen, White, Zelano, & Branigan

[57] ABSTRACT

The invention provides a higher alkoxy-substituted organopolysiloxane having, in a molecule, at least one alkoxy group of 4 to 30 carbon atoms bonded to the silicon atom excepting those at the molecular chain ends and still having a high degree of polymerization of at least 15. Such an organopolysiloxane, not known in the prior art, can be prepared by the dehydrogenation condensation reaction between an organohydrogenpolysiloxane and a higher aliphatic alcohol in the presence of a catalyst system consisting of a platinum compound and an organic acid such as acetic and citric acids. The higher alkoxy-substituted organopolysiloxane is useful as an additive in toiletry and cosmetic preparations by virtue of the good compatibility with other ingredients therein and high resistance against hydrolysis.

3 Claims, 3 Drawing Sheets

HIGHER ALKOXY-SUBSTITUTED ORGANOPOLYSILOXANE

CROSS REFERENCE TO RELATED APPLICATIONS

This is a continuation-in-part application from a co-pending U.S. patent application Ser. No. 07/973,530 filed Nov. 9, 1992, and now abandoned, which is a continuation application of a U.S. patent application Ser. No. 07/759,340 filed Sep. 13, 1991, now abandoned.

BACKGROUND OF THE INVENTION

The present invention relates to a novel organopolysiloxane compound. More particularly, the invention relates to a novel organopolysiloxane compound having, in a molecule, at least one alkoxy group having at least 4 or, preferably, at least 14 carbon atoms bonded to the silicon atom.

As is well known, organopolysiloxanes or so-called silicones have excellent properties including high chemical and physical stability as well as inherent inertness to the human body so that silicones or, in particular, silicone oils are widely used as an ingredient in a wide variety of toiletry and cosmetic preparations. For example, eaux de cologne, toiletry soaps, enamels for manicure and pedicure, lipsticks, lip creams, shampoos, hair rinses, eye shadows, eyeliners, mascaras, cheek rouges and the like are sometimes formulated with an organopolysiloxane such as a dimethyl polysiloxane oil, methyl phenyl polysiloxane oil, octamethyl cyclotetrasiloxane, decamethyl cyclopentasiloxane, methyl hydrogen polysiloxane oil and the like. Some of toiletry and cosmetic preparations are formulated with an organopolysiloxane having at least one alkoxy group bonded to the silicon atom in a molecule such as a dimethyl polysiloxane-methyl polyoxyethylene copolymer, dimethyl polysiloxane-methyl polyoxypropylene copolymer, dimethyl polysiloxane-methyl polyoxyethylenepropylene copolymer and the like.

The method for the preparation of the above mentioned organopolysiloxanes having silicon-bonded higher alkoxy groups is well known in the art of silicones. For example, Japanese Patent Publication No. 48-19941 teaches a method in which an organohydrogenpolysiloxane is subjected to a dehydrogenation condensation reaction with a higher alcohol in the presence of a strong alkali as the catalyst such as an alkali metal hydroxide and alkali metal alkoxide. Although the alkoxy residue of the higher alcohol can be bonded to the silicon atoms by this reaction, the siloxane linkages in the starting organohydrogenpolysiloxane are subject to the attack of the strong alkali used as the catalyst to cause scission so that the alkoxy group-containing organopolysiloxane obtained as the product necessarily has a greatly decreased degree of polymerization or number of the silicon atoms in a molecule of, for example, 10 or smaller. Accordingly, it is eagerly desired to obtain an organopolysiloxane having a sufficiently high degree of polymerization and containing higher alkoxy groups having, for example, at least 4 or, in particular, at least 14 carbon atoms in order to impart toiletry and cosmetic preparations with certain advantageous properties obtained only by formulating such a silicone having good compatibility with the other ingredients in the toiletry and cosmetic preparations.

An alternative method for the preparation of an alkoxy-substituted organopolysiloxane is the dehydrogenation condensation reaction between an organohydrogenpolysiloxane and an alcohol in the presence of a platinum compound as the catalyst. This platinum-catalyzed dehydrogenation reaction, however, can proceed only when the alcohol is a lower aliphatic alcohol such as methyl and ethyl alcohols and the reaction can hardly proceed when the alcohol is a higher alcohol having, for example, 4 or more or, in particular, 14 or more carbon atoms in a molecule.

SUMMARY OF THE INVENTION

The present invention accordingly has an object to provide a novel organopolysiloxane substituted by a higher alkoxy group and having a high degree of polymerization not known in the prior art nor described in any literatures.

Thus, the present invention provides a higher alkoxy-substituted diorganopolysiloxane represented by the general formula

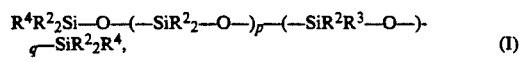

in which $R^2$ is, each independently from the others, an unsubstituted or substituted monovalent hydrocarbon group having 1 to 15 carbon atoms or, preferably, a methyl group, $R^3$ is an alkoxy group having 4 to 30 or, preferably, 14 to 18 carbon atoms, $R^4$ is $R^2$ or $R^3$, the subscript p is zero or a positive integer and the subscript q is a positive integer with the pro-viso that p+q is 13 or larger.

The above defined novel higher alkoxy-substituted dirorganopolysiloxane can be prepared, for example, by the method in which an organohydrogenpolysiloxane represented by the general formula

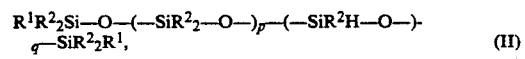

in which $R^2$ has the same meaning as defined above, $R^1$ is a hydrogen atom directly bonded to the silicon atom or $R^2$ and the subscripts p and q each have the same meaning as defined above, is subjected to a dehydrogenation condensation reaction with an aliphatic alcohol represented by the general formula

in which $R^3$ has the same meaning as defined above, in the presence of a platinum compound and an organic acid such as acetic acid and citric acid.

DETAILED DESCRIPTION OF THE PREFERRED EMBODIMENTS

Figure 1:
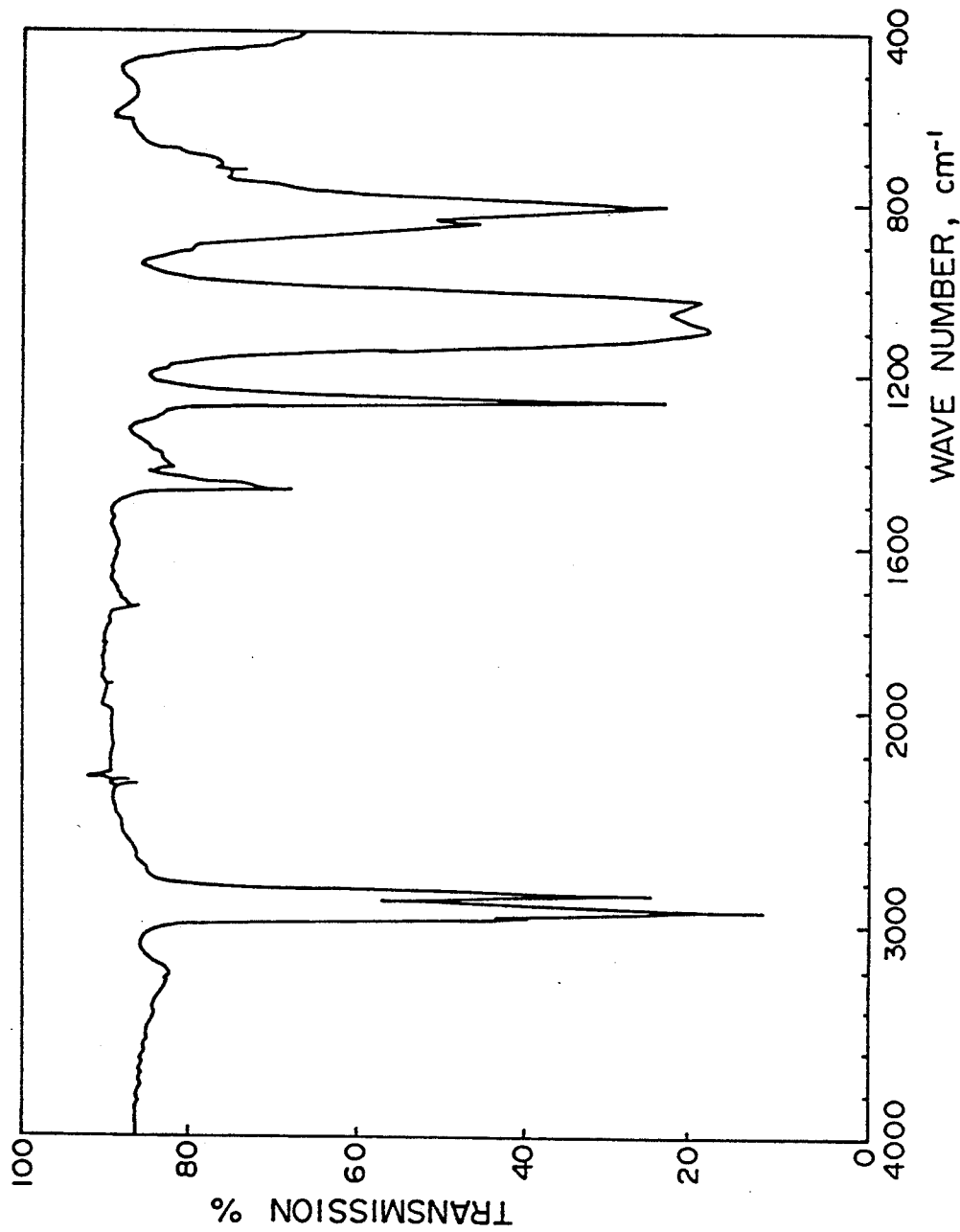
FIG. 1 shows an infrared absorption spectrum of the alkoxy-substituted organopolysiloxane prepared in Example 1 and FIGS. 2 and 3 are each a diagram of $^{13}$C-NMR spectrum of the same.

As is described above, the present invention provides a novel alkoxy-substituted diorganopolysiloxane having, in a molecule, at least one higher alkoxy group of 4 to 30 or, preferably, 14 to 18 carbon atoms and a high degree of polymerization of at least 15 as is defined by the above given general formula (I). Such an alkoxy-substituted diorganopolysiloxane of the general formula (I) is a novel compound not known in the prior art nor described in any literatures. For example, U.S. Pat. No. 4,731,411 broadly discloses an alkoxy-substituted diorganopolysiloxane, of which the alkoxy group has 1 to 8 carbon atoms, although no actual examples are given there for the alkoxy groups having 2 or more carbon atoms, and the methoxy groups as the sole species of the alkoxy groups are always bonded to the silicon atoms at the molecular chain ends. In contrast thereto, the most characteristic feature of the inventive alkoxy-substituted diorganopolysiloxane consists in that at least one of the silicon atoms excepting those at the molecular chain ends has a higher alkoxy group bonded thereto. It is a quite unexpected surprising discovery that such an inventive alkoxy-substituted diorganopolysiloxane has greatly improved compatibility with certain ingredients frequently formulated in toiletry and cosmetic preparations such as stearyl alcohol as compared with diorganopolysiloxanes having lower alkoxy groups bonded only to the terminal silicon atoms. The compatibility of the inventive higher alkoxy-substituted diorganopolysiloxane with stearyl alcohol is still better when the silicon atoms at the molecular chain ends have no higher alkoxy groups bonded thereto, i.e. when $R^4$ is $R^2$ in the above given general formula (I). In addition, the higher alkoxy groups bonded to the silicon atoms in the diorganopolysiloxane according to the invention are highly resistant against hydrolysis as compared with lower silicon-bonded alkoxy groups such as methoxy disclosed in the above mentioned U.S. patent. This stability against hydrolysis is particularly important when the intended application of the alkoxy-substituted diorganopolysiloxane is as an additive in toiletry or cosmetic preparations, most of which contain water more or less as one of the essential ingredients.

The inventive alkoxy-substituted diorganopolysiloxane can be readily prepared by the dehydrogenation condensation reaction between an organohydrogenpolysiloxane of the general formula (II) and a higher aliphatic alcohol of the general formula (III) in the presence of a platinum compound as the catalyst and an organic acid such as acetic acid which may serve as a co-catalyst. This method is also unique as compared with the method disclosed in U.S. Pat. No. 4,731,411, in which a silanol-terminated diorganopolysiloxane and an alkoxy-containing organohydrogensilane are subjected to the dehydrogenation reaction in the presence of a platinum catalyst.

The novel alkoxy-substituted diorganopolysiloxane of the invention is represented by the above given general formula (I). In the formula, $R^2$ is an unsubstituted or substituted monovalent hydrocarbon group of 1 to 15 carbon atoms exemplified by alkyl groups such as methyl, ethyl, propyl and butyl groups, cycloalkyl groups such as cyclohexyl group, alkenyl groups such as vinyl and allyl groups and aryl groups such as phenyl and tolyl groups as well as those substituted groups such as chloromethyl, 3,3,3-trifluoropropyl and 2-cyanoethyl groups obtained by replacing a part or all of the hydrogen atoms in the above named hydrocarbon groups with halogen atoms, cyano groups and the like. The group denoted by $R^3$ is a higher alkoxy group having 4 to 30 or, preferably, 14 to 18 carbon atoms exemplified by butoxy, pentoxy, hexoxy, octoxy, myristyloxy, cetyloxy, oleyloxy and stearyloxy groups. The group denoted by $R^4$ is $R^2$ or $R^3$. The subscript p in the formula (I) is zero or a positive integer and the subscript q is a positive integer with the proviso that p+q is 13 or larger thus to give a degree of polymerization of the molecule of at least 15. Since the subscript q cannot be equal to zero, the inventive diorganopolysiloxane has at least one silicon atom, excepting the terminal silicon atoms, to which a higher alkoxy group is bonded.

The organohydrogenpolysiloxane as one of the starting reactants in the dehydrogenation reaction is represented by the general formula (II) given above, in which $R^5$ is a hydrogen atom or $R^2$, the symbols $R^2$, p and q each having the same meaning as defined above. Since the subscript q cannot be equal to zero, at least one of the silicon atoms excepting those at the molecular chain ends has a hydrogen atom directly bonded thereto.

The higher aliphatic alcohol to be reacted with the above defined organohydrogenpolysiloxane is represented by the above given general formula (III), in which $R^3$ has the same meaning as defined above. Examples of the aliphatic alcohols to be reacted with the organohydrogenpolysiloxane include butyl alcohol, hexyl al-cohol, octyl alcohol, myristyl alcohol, cetyl alcohol, oleyl alcohol, stearyl alcohol and the like and the alcohol should be selected among the above depending on the particular object of application of the alkoxy-substituted diorganopolysiloxane. When the intended application of the inventive alkoxy-substituted diorganopolysiloxane is as an additive in a toiletry or cosmetic preparation, those having a relatively large number of carbon atoms in a molecule, such as myristyl, cetyl and stearyl alcohols, are preferred in order to meet the requirements under statutory regulations for the formulation of those preparations still satisfying the requirement for the compatibility with other ingredients conventionally formulated in toiletry and cosmetic preparations as well as resistance against hydrolysis.

The amount of the above defined higher aliphatic alcohol to be reacted with the organohydrogenpolysiloxane should be at least equimolar to the silicon-bonded hydrogen atoms in the organohydrogenpolysiloxane. The amount of the alcohol is usually in the range from 1.0 to 1.3 moles per mole of the silicon-bonded hydrogen atoms in the organohydrogenpolysiloxane. When an excess amount of the alcohol is used relative to the organohydrogenpolysiloxane, the reaction mixture after completion of the reaction naturally contains a remaining amount of the unreacted alcohol which, however, usually is not detrimental and need not be removed from the reaction mixture at least when the intended application of the inventive alkoxy-substituted organopolysiloxane is as an additive in toiletry or cosmetic preparations.

The dehydrogenation reaction between the above described organohydrogenpolysiloxane and higher aliphatic alcohol is promoted by a catalyst system consisting of a platinum compound and an organic acid. The platinum compounds suitable for the purpose include those known ones conventionally used as a catalyst in the dehydrogenation reaction with a lower alcohol or in the hydrosilation reaction. For example, chloroplatinic acid and complexes thereof with an olefin or a vinyl-containing organopolysiloxane can be used. The amount of the platinum compound in the reaction mixture is usually in the range from 0.0001 to 0.1 part by weight calculated as platinum metal per 100 parts by weight of the organohydrogenpolysiloxane. The organic acid as the co-catalyst for the platinum compound in the catalyst system can be any of those compounds having a carboxyl group or phenolic hydroxy group in a molecule exemplified by formic acid, acetic acid, propionic acid, butyric acid, oxalic acid, citric acid, benzoic acid, phenol and the like, of which a carboxylic acid or, in particular, acetic acid is preferred.

Although the exact mechanism by which the dehydrogenation reaction of an organohydrogenpolysiloxane with an alcohol can proceed so smoothly even with a higher alcohol of 4 to 30 carbon atoms in a molecule is not fully understood, following is a presumable mechanism therefor taking a carboxylic acid RCOOH, in which R is an alkyl group, as the organic acid. Namely, the dehydrogenation reaction first takes place between the silicon-bonded hydrogen atoms and molecules of the carboxylic acid in the presence of the platinum catalyst according to the following reaction equation:

to give an acyloxy-substituted organopolysiloxane which is then reacted with the higher aliphatic alcohol $R^3H$ to cause exchange of the acyloxy group R—CO—O— with the alkoxy group $R^3$ according to the reaction equation:

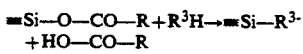

thus to regenerate the carboxylic acid.

Assuming that the above described mechanism of the reaction is actually held, it would be a possible way to conduct the reaction in such a stepwise manner that the organohydrogenpolysiloxane is first reacted with a carboxylic acid in an amount at least equimolar to the silicon-bonded hydrogen atoms therein to be converted into the acyloxy-substituted organopolysiloxane which is then reacted with the higher aliphatic alcohol to effect the exchange reaction of the acyloxy groups and the alkoxy groups. A more advantageous way, however, is that a reaction mixture is formed by mixing the higher aliphatic alcohol, organic acid, platinum compound and, if necessary, organic solvent and then the organohydrogenpolysiloxane is added dropwise to the reaction mixture so that the dehydrogenation reaction and the exchange reaction may proceed concurrently in a one-step procedure. Alternatively, a reaction mixture is formed by mixing the organohydrogenpolysiloxane, alcohol, platinum compound and, if necessary, organic solvent and the organic acid is added thereto dropwise.

The amount of the organic acid added to the reaction mixture is in the range from 0.01 to 3 moles per mole of the silicon-bonded hydrogen atoms in the organohydrogenpolysiloxane. Since the organic acid can be regenerated by the exchange reaction of the acyloxy groups with the alkoxy groups as is described above, however, the amount is preferably in the range from 0.1 to 1.0 mole per mole of the silicon-bonded hydrogen atoms in the organohydrogenpolysiloxane.

Although the reaction can proceed without diluting the reaction mixture with an organic solvent, it is sometimes advantageous in order to ensure more smooth proceeding of the reaction that the reaction mixture is admixed with an organic solvent. The organic solvent, when used, must be one having no active hydrogen atom in the molecule in order not to disturb the dehydrogenation reaction between the reactants. Examples of suitable organic solvents include aliphatic hydrocarbon solvents such as hexane and heptane, aromatic hydrocarbon solvents such as toluene and xylene, esters and ethers such as ethyl acetate and dibutyl ether and chlorinated hydrocarbon solvents such as trichloroethylene and trichloroethane.

The dehydrogenation reaction proceeds when the reaction mixture is heated at a temperature in the range from 30° to 150° C. or, preferably, from 60° to 80° C. When the reaction temperature is too low, the velocity of the reaction would be too low as a matter of course taking an unduly long time for completion of the reaction. When the reaction temperature is too high, on the other hand, undesirable side reactions, such as the esterification reaction between the alcohol and the organic acid, may take place to cause a decrease in the yield of the desired product. The reaction is usually complete within 10 to 20 hours when the reaction temperature is in the range from 60° to 80° C.

After completion of the reaction, the reaction mixture is washed with water to remove the organic acid followed by stripping of the organic solvent, when used, by distillation under reduced pressure to give the desired higher alkoxy-substituted organopolysiloxane. It is a possible way that, in place of washing of the reaction mixture with water, the organic acid is removed by distillation under reduced pressure together with the organic solvent when the organic acid has a relatively low boiling point as acetic acid. When the organic acid has a relatively high boiling point or is non-volatile as citric acid, removal of such an organic acid from the reaction product is in most cases not requisite since such an organic acid has no particular adverse effect on the human body when the reaction mixture obtained by the reaction is used as such as an additive in toiletry and cosmetic preparations.

In the following, the higher alkoxy-substituted diorganopolysiloxane of the invention is described in more detail by way of examples.

EXAMPLE 1

Into a reaction vessel of 5 liters capacity were introduced 1485 g (5.5 moles) of stearyl alcohol, 300 g (5.0 moles) of acetic acid, 600 g of toluene and 3 g of a 0.05% by weight solution of a vinylsiloxane complex of chloroplatinic acid in toluene to form a mixture, into which 1202 g (1 mole) of a methyl hydrogen polysiloxane expressed by the average formula

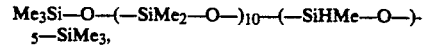

in which Me is a methyl group, were added dropwise while the mixture in the reaction vessel was heated and kept at 60° C. under a stream of nitrogen gas. After completion of the dropwise addition of the methyl hydrogen polysiloxane, the reaction mixture in the vessel was further agitated at the same temperature for 15 hours. The reaction mixture was then analyzed for the residual content of the silicon-bonded hydrogen atoms in the methyl hydrogen polysiloxane by decomposing and converting the silicon-bonded hydrogen atoms into free hydrogen gas. The result was that the volume of the hydrogen gas evolved in the analysis was 0.2 ml/g at N.T.P. indicating that at least 99% of the silicon-bonded hydrogen atoms in the starting methyl hydrogen polysiloxane had reacted in the dehydrogenation reaction.

Figure 2:
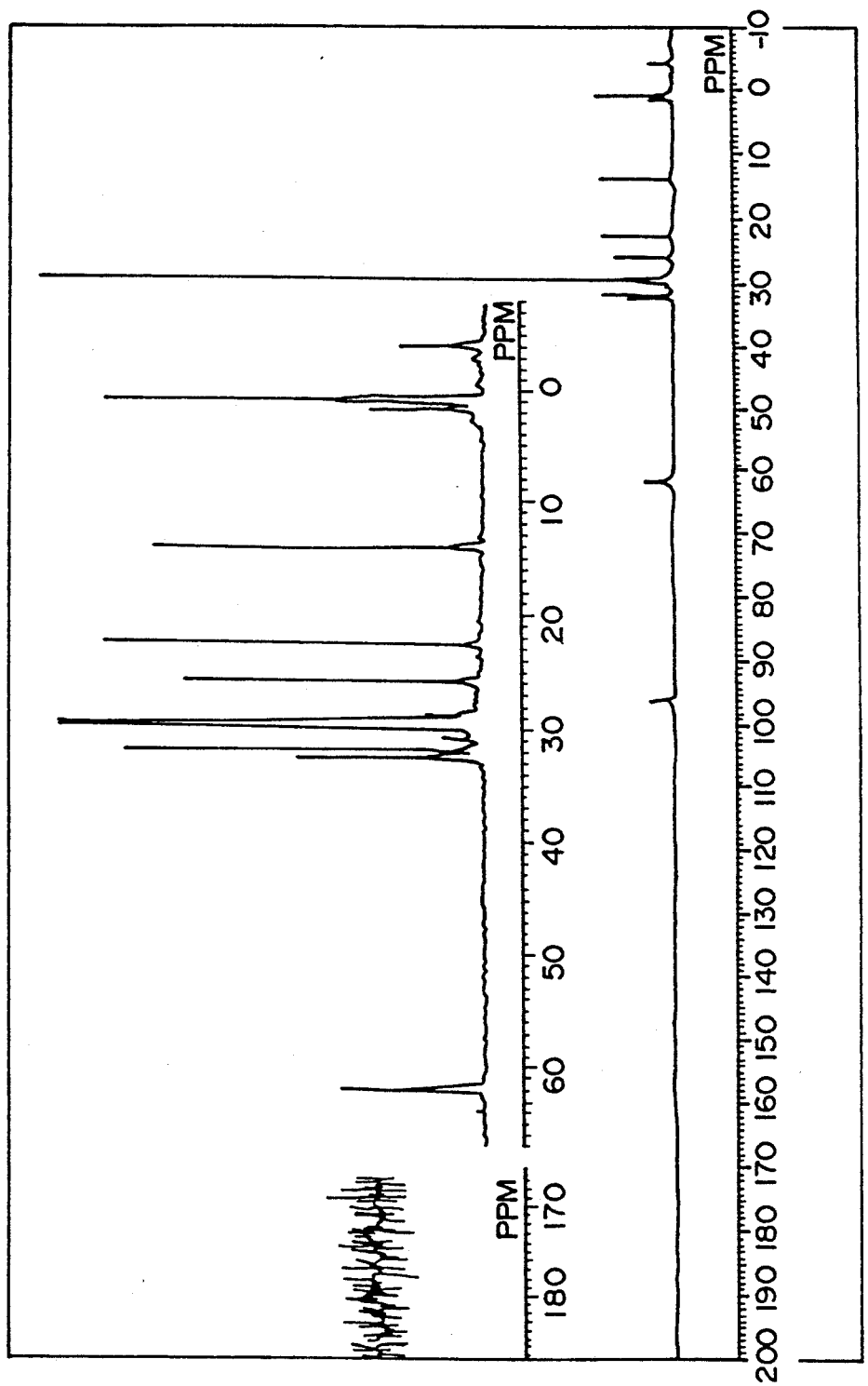
Figure 3:
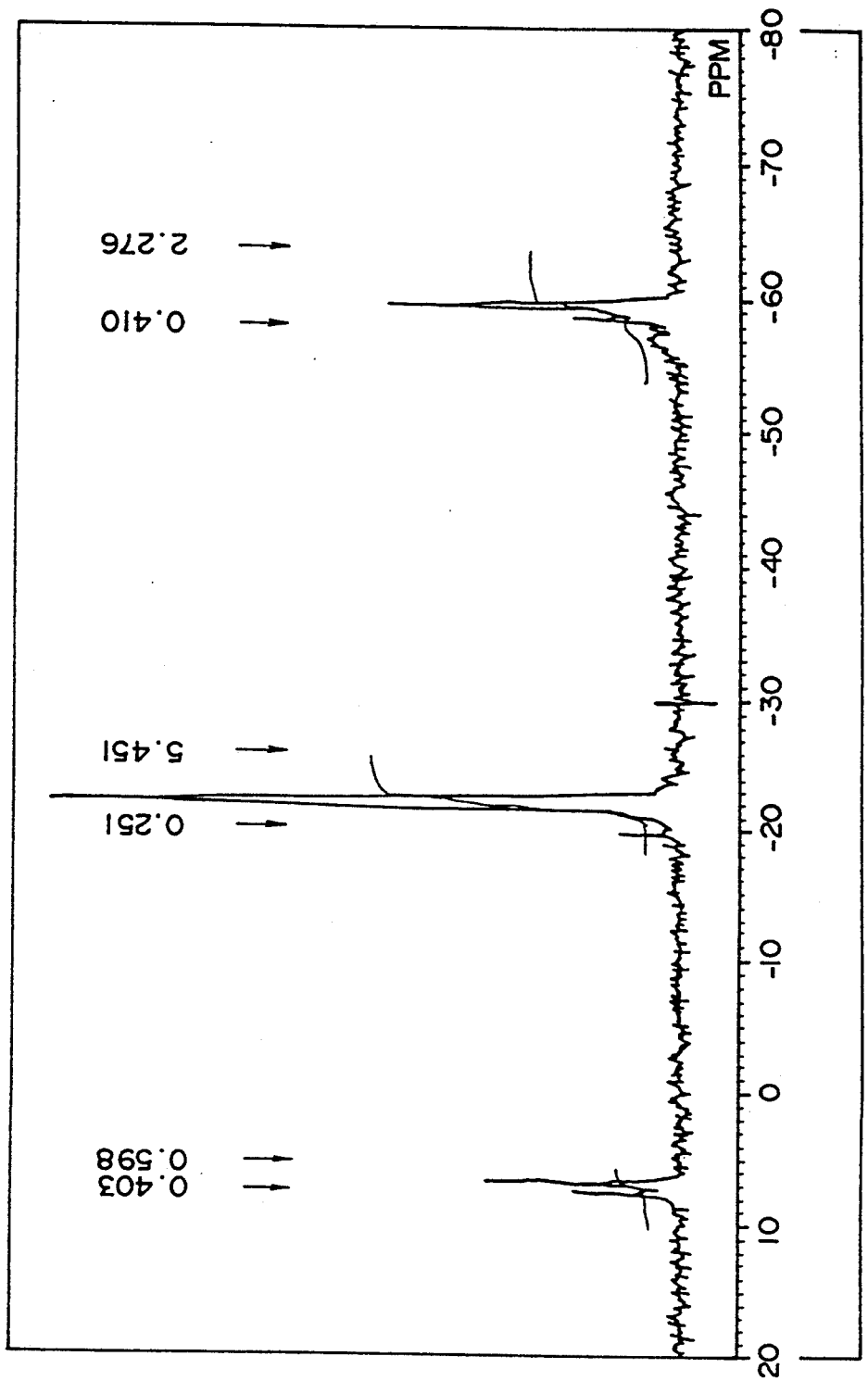

In the next place, the thus obtained reaction mixture was washed three times each with 600 ml of water to be freed from acetic acid and further stripped at 150° C. under reduced pressure to be freed from toluene followed by cooling to give 2576 g of a greyish solid as the product corresponding to 96% of the theoretical yield. This product could be melted within a temperature range of which the temperature for complete melting was 44° C. The melt of the product had a viscosity of 24 centistokes at 60° C. This product was subjected to the measurements of the infrared absorption spectrum and $^{13}$C-NMR spectrum to give the results shown in FIG. 1 for the infrared absorption spectrum and FIGS. 2 and 3 for the NMR spectrum. These analytical results supported the conclusion that the product obtained was a stearyloxy-substituted organopolysiloxane expressed by the average formula

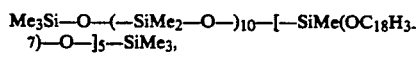
Me$_3$Si—O—(—SiMe$_2$—O—)$_{10}$—[—SiMe(OC$_{18}$H$_{37}$)—O—]$_5$—SiMe$_3$, in which Me is a methyl group.

The above prepared stearyloxy-substituted diorganopolysiloxane was tested for the stability against hydrolysis. Thus, the diorganopolysiloxane, water and a non-ionic surface active agent having an HLB value of 4.5 were mixed together in a weight proportion of 2:4:1 to form an aqueous emulsion, which was kept standing at 50° C. or 60° C. in a hermetically sealed container and the percentage of the hydrolyzed stearyloxy groups was analytically determined periodically over 3 months. The results obtained at the end of the 3-months period were that only about 5% and about 11% of the stearyloxy groups had been hydrolyzed at 50° C. and 60° C., respectively.

In order to test the compatibility of the above prepared stearyloxy-substituted diorganopolysiloxane with an ingredient in a conventional toiletry or cosmetic preparation, the stearyloxy-substituted diorganopolysiloxane was mixed with stearyl alcohol by heating at 70° C. in a 1:1 weight ratio to give a completely clear mixture to indicate good miscibility therebetween.

COMPARATIVE EXAMPLE

A comparative stearyloxy-substituted diorganopolysiloxane was prepared in the following manner. Thus, a mixture was prepared by mixing 250 g of dehydrated toluene, 4.8 g (0.08 mole) of acetic acid and 0.1 g of an isopropyl alcohol solution of chloroplatinic acid in a concentration of 2% by weight as platinum metal and the mixture was heated and kept at 100° C. under agitation in a flask equipped with a reflux condenser. Into the mixture in the flask, 250 g (0.033 mole) of a methyl hydrogen polysiloxane expressed by the average formula

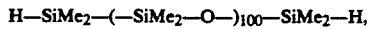
H—SiMe$_2$—(—SiMe$_2$—O—)$_{100}$—SiMe$_2$—H, in which Me is a methyl group were added dropwise followed by further continued agitation of the mixture in the flask for additional 4 hours at 100° C. to complete the dehydrogenation reaction. The analysis of the reaction mixture for the silicon-bonded hydrogen atoms indicated that the dehydrogenation reaction had proceeded almost completely. Thereafter, 23.3 g (0.086 mole) of stearyl alcohol were added to the mixture which was further agitated at 100° C. for additional 2 hours. The reaction mixture was then stripped under reduced pressure at 150° C. to be freed from volatile matters including toluene and acetic acid followed by cooling to room temperature. The thus obtained white product had a pasty consistency and could be identified to be expressed by the average formula

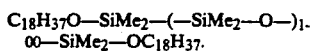
C$_{18}$H$_{37}$O—SiMe$_2$—(—SiMe$_2$—O—)$_{100}$—SiMe$_2$—OC$_{18}$H$_{37}$.

This stearyloxy-substituted dimethylpolysiloxane was tested for the compatibility with stearyl alcohol in the same manner as in Example 1 to find that the 1:1 by weight mixture was completely opaque in white color indicating that the dimethylpolysiloxane was immiscible with stearyl alcohol.

EXAMPLE 2

Into a reaction vessel of 5 liters capacity were introduced 972 g (3.8 moles) of stearyl alcohol, 98 g (0.5 mole) of citric acid, 200 g of toluene and 2 g of a 0.5% by weight solution of a vinylsiloxane complex of chloroplatinic acid in toluene to form a mixture, into which 2340 g (1 mole) of a methyl hydrogen polysiloxane expressed by the average formula

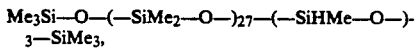
Me$_3$Si—O—(—SiMe$_2$—O—)$_{27}$—(—SiHMe—O—)$_3$—SiMe$_3$, in which Me is a methyl group, were added dropwise while the mixture in the reaction vessel was heated and kept at 70° C. under a stream of nitrogen gas. After completion of the dropwise addition of the methyl hydrogen polysiloxane, the reaction mixture in the vessel was further agitated at the same temperature for 10 hours to complete the reaction. The reaction mixture was then analyzed for the residual content of the silicon-bonded hydrogen atoms in the methyl hydrogen polysiloxane by decomposing and converting the silicon-bonded hydrogen atoms into free hydrogen gas. The result was that almost no hydrogen gas was evolved indicating that the dehydrogenation reaction was almost complete.

In the next place, the thus obtained reaction mixture was washed three times each with 400 ml of water to be freed from citric acid and further stripped at 150° C. under reduced pressure to be freed from toluene followed by cooling to give 3140 g of a greyish solid as the product corresponding to 95% of the theoretical yield. This product could be melted within a temperature range of which the temperature for complete melting was 41° C. The melt of the product had a viscosity of 18 centistokes at 60° C. This product was subjected to the measurements of the infrared absorption spectrum and $^{13}$C-NMR spectrum to give the results which supported the conclusion that the product obtained was a stearyloxy-substituted organopolysiloxane expressed by the average formula

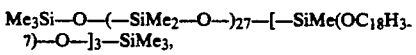
Me$_3$Si—O—(—SiMe$_2$—O—)$_{27}$—[—SiMe(OC$_{18}$H$_{37}$)—O—]$_3$—SiMe$_3$, in which Me is a methyl group.

EXAMPLE 3

The experimental procedure was substantially the same as in Example 1 except that the stearyl alcohol was replaced with 1331 g (5.5 moles) of cetyl alcohol to give 2340 g of a greyish solid product in a yield of 93% of the theoretical value. The temperature of complete melting of this solid was 37° C. and the melt of the solid had a viscosity of 19 centistokes at 60° C.

The results of the infrared absorption spectrophotometry and NMR spectroscopy supported the conclusion that this product was a cetyloxy-substituted organopolysiloxane expressed by the average formula

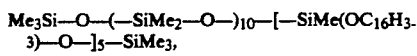

$$Me_3Si-O-(-SiMe_2-O-)_{10}-[-SiMe(OC_{16}H_{33})-O-]_5-SiMe_3,$$

in which Me is a methyl group.

EXAMPLE 4

The experimental procedure was substantially the same as in Example 1 except that the stearyl alcohol was replaced with 1177 g (5.5 moles) of myristyl alcohol to give 2270 g of a light yellow liquid product in a yield of 96% of the theoretical value. This liquid product had a viscosity of 41 centistokes at 25° C.

The results of the infrared absorption spectrophotometry and NMR spectroscopy supported the conclusion that this product was a myristyloxy-substituted organopolysiloxane expressed by the average formula

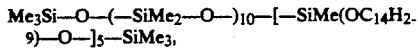

$$Me_3Si-O-(-SiMe_2-O-)_{10}-[-SiMe(OC_{14}H_{29})-O-]_5-SiMe_3,$$

in which Me is a methyl group.

What is claimed is:

1. A method for the preparation of a higher alkoxy-substituted diorganopolysiloxane represent-ed by the general formula

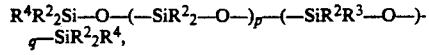

$$R^4R^2_2Si-O-(-SiR^2_2-O-)_p-(-SiR^2R^3-O-)_q-SiR^2_2R^4,$$

in which $R^2$ is, each independently from the others, an unsubstituted or substituted monovalent hydrocarbon group having 1 to 15 carbon atoms, $R^3$ is an alkoxy group having 4 to 30 carbon atoms, $R^4$ is $R^2$ or $R^3$, the subscript p is zero or a positive integer and the subscript q is a positive integer with the proviso that p+q is 13 or larger, which comprises: subjecting an organohydrogenpolysiloxane represented by the general formula

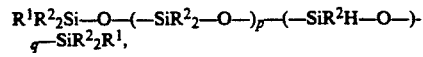

$$R^1R^2_2Si-O-(-SiR^2_2-O-)_p-(-SiR^2H-O-)_q-SiR^2_2R^1,$$

in which $R^2$ has the same meaning as defined above, $R^1$ is a hydrogen atom directly bonded to the silicon atom or $R^2$ and the subscripts p and q each have the same meaning as defined above, and an aliphatic alcohol represented by the general formula

$$R^3H,$$

in which $R^3$ has the same meaning as defined above, to a dehydrogenation reaction in the presence of a platinum compound and an organic acid.

2. The method as claimed in claim 1 in which the organic acid is a carboxylic acid.

3. The method as claimed in claim 1 in which the amount of the organic acid is in the range from 0.01 to 3 moles per mole of the silicon-bonded hydrogen atoms in the organohydrogenpolysiloxane.

* * * * *